United States Patent
Formelli (10) Patent No.: US 7,169,813 B2
(45) Date of Patent: Jan. 30, 2007

(54) 4-OXO-FENRETINIDE, ADMINISTERED ALONE AND IN COMBINATION WITH FENRETINIDE, AS PREVENTIVE AND THERAPEUTIC AGENT FOR CANCER

(75) Inventor: Franca Formelli, Milan (IT)

(73) Assignee: Fondazione IRCCS "Istituto Nazionale Dei Tumori" (IT)

( * ) Notice: Subject to any disclaimer, the term of this patent is extended or adjusted under 35 U.S.C. 154(b) by 0 days.

(21) Appl. No.: 10/557,311

(22) PCT Filed: Mar. 18, 2004

(86) PCT No.: PCT/IB2004/000789

§ 371 (c)(1),
(2), (4) Date: Jul. 25, 2006

(87) PCT Pub. No.: WO2005/092314

PCT Pub. Date: Oct. 6, 2005

(65) Prior Publication Data

US 2006/0264514 A1    Nov. 23, 2006

(51) Int. Cl.
*A61K 31/195* (2006.01)
*C07C 233/09* (2006.01)

(52) U.S. Cl. ............. 514/563; 554/65; 564/161; 514/617

(58) Field of Classification Search ........... 514/563, 514/617; 554/65; 564/161
See application file for complete search history.

(56) References Cited

U.S. PATENT DOCUMENTS 6,696,606 B1 * 2/2004 Curley et al. ............... 564/142

OTHER PUBLICATIONS

Ulukaya E et al. "Fenretinide and its relation to cancer" Cancer Treatment Reviews, Saunders, US, vol. 25, No. 4, Aug. 1999, pp. 229-235, XP008009394 ISSN: 0305-7372.

Mehta R R et al.: "Metabolism of N-(4-hydroxpheny) retinamide (4-HPR) to N-(4-methyoxphenyl) retinamide (4-MPR) may serve as a biomarker for its efficacy against human breast cancer and melanoma cells" European Journal of Cancer, vol. 34, No. 6, May 1998, pp. 902-907, XP002303841 ISSN: 0959-8049 abstract.

Apprierto V et al.: "Decrease in drug accumulation and in tumor aggressiveness marker expression in a fenretinide-induced resistant ovarian tumor cell line." British Journal of Cancer. Jun. 1, 2001, vol. 84, No. 11, Jun. 1, 2001, pp. 1528-1534, XP002303842 ISSN: 0007-0920 abstract p. 1528, left-hand column.

Ozols Robert F et al.: "Specific keynote: Chemoprevention of ovarian cancer: The journey begins." Gynecologic Oncology, vol. 88, No. 1 Part 2, Jan. 2003, pp. S59-S66, XP002303843 ISSN: 0090-8258 p. S62, last paragraph-p. S63, paragraph 1.

Ribatti Domenico et al.: "Fenretinide as an anti-angiogenic agent in neuroblastoma." Cancer Letters, vol. 197, No. 1-2, Jul. 18, 2003, pp. 181-184, XP002303844 ISSN: 0304-3835 abstract.

* cited by examiner

*Primary Examiner*—Shailendra Kumar
(74) *Attorney, Agent, or Firm*—Greenberg Traurig, LLP; R. Joseph Foster, Esq.

(57) ABSTRACT

A drug based on a metabolite of fenretinide, or N-(4hydroxyphenyl) retinamide (4-HPR), specifically 4-oxo-N-(4-hydroxyphenyl) retinamide (4-oxo-4-HPR), is used in the treatment of different kinds of tumors, in particular in the treatment of ovarian carcinoma, breast tumor and neuroblastoma. The drug is more potent than fenretinide alone, and enhances the effects of fenretinide when administered together with fenretinide.

7 Claims, 6 Drawing Sheets

Fig. 1

Fig.2 Ovarian Tumor Cell Lines

Fig.3 Breast Tumor Cell Lines

APOPTOSIS ASSAY

Fig. 6

4-OXO-FENRETINIDE, ADMINISTERED ALONE AND IN COMBINATION WITH FENRETINIDE, AS PREVENTIVE AND THERAPEUTIC AGENT FOR CANCER

This application is a national stage filing under 35 U.S.C. 371 of International Application PCT/IB2004/000789 filed on Mar. 18, 2004. International Application PCT/IB2004/000789 was published under PCT Article 21(2) in English.

TECHNICAL FIELD

The present invention relates to the clinical use of one of the metabolites of the synthetic retinoid fenretinide, which is known to have antitumor properties. In particular it relates to the use of the metabolite 4-oxo-fenretinide for preventing and treating cancer and for its use in combination with fenretinide in order to improve fenretinide activity and/or to overcome fenretinide resistance.

BACKGROUND OF THE INVENTION

Retinoids are natural and synthetic derivatives of vitamin A (retinol), which modulate different cellular processes, including proliferation, differentiation and apoptosis. They are compounds of clinical interest for the treatment and prevention of a variety of tumors. Fenretinide, or N-(4-hydroxyphenyl)retinamide (4-HPR), is a synthetic retinoid (an amide of all-trans retinoic acid), which, in preclinical models, proved to be less toxic than many other retinoids while maintaining a significant biological activity. (Moon et al., Cancer Res., 1979, 39:1339–1346). In animal models, 4-HPR had preventive efficacy in mammary, prostate and colon carcinogenesis and lymphomagenesis and therapeutic efficacy against neuroblastoma, mammary, ovary and Kaposi's tumors (Formelli et al., FASEB J. 1996, 10:1014–1024; Ferrari et al., Clin. Cancer Res. 2003, 9:6020–6029). In clinical trials in adults (Veronesi et al., J. Natl. Cancer Inst. 1999, 91:1847–56) and in children (Garaventa et al., Clin. Cancer Res. 2003, 9:2032–2039), 4-HPR had a favorable toxicity profile and was better tolerated than other retinoids. Its main side effect was impaired dark adaptation, which was due to reduction of retinol plasma levels (Formelli et al., Cancer Res. 1989, 49:6149–6152). In humans, 4-HPR has shown efficacy in premalignant lesions such as oral leucoplakia (Chiesa et al., Oral Oncol. Europ. J. Cancer, 1992, 28B(2):97–102), lichen planus (Tradati at al., Cancer Lett., 1994, 76:109–111) and actinic keratoses (Moglia et al., Cancer Lett. 1996, 110:87–91) and has shown promising results for the prevention of breast and ovarian tumors (Veronesi et al., J. Natl. Cancer Inst. 1999, 91:1847–56; De Palo et al., Gynecol. Oncol., 2002, 86:24–27). In a clinical trial in women treated with 4-HPR after having undergone surgery for early breast cancer, 4-HPR reduced the incidence of new breast cancer in premenopausal women (Veronesi et al., J. Natl. Cancer Inst. 1999, 91:1847–56). In the same trial, a significant reduction in the incidence of ovarian cancer was also observed during the treatment period (De Palo et al., Gynecol. Oncol., 2002, 86:24–27). Actually, the retinoid is under investigation as a preventive and therapeutic agent for neuroblastoma, breast and ovarian tumors.

The tumor preventive and therapeutic activity of 4-HPR has been attributed to its potent growth inhibitory effects, associated with induction of apoptosis, which have been shown in tumor cells of different histiotypes, including breast, prostate, ovary, head and neck, neuroblastoma and leukemia (Formelli et al., FASEB J. 1996, 10:1014–1024).

Considerable attention has been directed towards understanding the mechanism of action of this retinoid and different molecular targets have been implicated in its growth inhibitory activity.

An important aspect that may contribute to the biological effects of 4-HPR is its metabolism. It is known that 4-HPR is extensively metabolized in vivo (Hultin et al.,. Drug Metab. Dispos., 1986, 14:714–717; Formelli et al., Cancer Res., 1989, 49:6149–6152; Mehta et al., Eur. J. Cancer, 1991, 27:138–141), but it is not known whether 4-HPR or one of its metabolites is the active agent and how they interact with each other. Moreover, nothing is known about 4-HPR metabolism in tumor cells. To date, the only identified metabolite of 4-HPR is N-(4-methoxyphenyl)retinamide (4-MPR), which is less polar than the parent drug and which has been found in all the in vivo studies in mice, rats and humans. 4-MPR does not seem to play a role in 4-HPR tumor growth inhibitory effect because it was ineffective in inhibiting proliferation in different tumor cell lines (Appierto et al., Br. J. Cancer., 2001, 84:1528–1534; Metha et al., Eur. J. Cancer, 1998, 34:902–907). Moreover, in mice bearing a human ovarian carcinoma, 4-MPR had no antitumor effect and it did not increase 4-HPR activity (Formelli et al., Eur. J. Cancer, 2000, 36:2411–2419). In addition to 4-MPR, all the indicated studies also reported the presence of unidentified metabolites more polar than the parent drug. In one of these studies, it was found that in normal and tumor breast tissues of women treated with 4-HPR, 4-MPR was mainly localized in the fat tissue, whereas 4-HPR and an unidentified polar metabolite were concentrated in epithelial cells, that is in the cells where the drug is supposed to exert its effect (Metha et al., Eur. J. Cancer, 1991, 27: 138–141).

SUMMARY OF THE INVENTION

The present invention provides a metabolite of fenretinide, or N-(4-hydroxyphenyl)retinamide (4-HPR), specifically 4-oxo-N-(4-hydroxyphenyl)retinamide (4-oxo-4-HPR) of the following formula:

Chemical formula: $C_{26}H_{31}NO_3$
Molecular weight: 405 for treatment and prevention of cancer and for improving and/or overcoming fenretinide resistance.

4-oxo-4-HPR, is a polar metabolite of 4-HPR, which was identified in tumor cells treated with the retinoid and in plasma samples collected from patients enrolled in 4-HPR clinical trials.

The molecule was synthesized and in in vitro grown tumor cells 4-oxo-HPR had a strong antiproliferative activity in 4-HPR-sensitive and -resistant cells, was more potent than 4-HPR, and it was synergic with 4-HPR.

Administered to mice, 4-oxo-HPR caused a slight reduction of retinol plasma levels, which was lower than that caused by 4-HPR. It is therefore an object of the present invention to provide 4-oxo-4-HPR which is effective in tumor cells, including those resistant to 4-HPR, and whose effects on retinol are lower than those of 4-HPR, for preventing and treating the development of malignant lesions. In addition, the results of the two retinoids in combination indicate a way to improve 4-HPR activity and/or to overcome 4-HPR resistance.

DETAILED DESCRIPTION OF THE INVENTION

The present invention provides a drug that may be used for the prevention and treatment of cancer, that is a metabolite of the antitumor agent 4-HPR, specifically 4-oxo-HPR, that is more potent and with a wider range of tumor cell growth inhibitory activity than the parent drug.

The compound may be identified in tumor cells and in blood samples of patients treated with 4-HPR and synthesized according to the following examples.

Identification of 4-oxo-4-HPR

EXAMPLE 1

We have previously reported that in plasma of patients treated with 4-HPR (Formelli et al., Cancer Res., 1989, 49:6149–6152) and in A2780/HPR human ovarian carcinoma cells, obtained from A2780 cells after continuous exposure to 5 μM 4-HPR (Appierto et al., Br. J. Cancer, 2001, 84:1528–1534), besides the parent drug 4-HPR and the metabolite 4-MPR, another metabolite, more polar than the parent drug, was present. Here we describe how the metabolite can be identified.

The presence of 4-HPR and its metabolites in plasma, culture medium and tumor cell extracts was evaluated by high pressure liquid chromatography (HPLC) as previously described (Formelli et al., Cancer Res., 1989, 49:6149–6152). Briefly, plasma samples were obtained from blood collected 12 h after the last daily 4-HPR dose from patients participating in a breast cancer prevention trial (Formelli et al. Cancer Res., 1989, 49: 6149–6152). A2780/HPR -cell pellets and -media were collected 72 h after treatment with 5 μM 4-HPR (Appierto et al., Br. J. Cancer, 2001, 84:1528–1534). All the procedures were performed with the samples protected from light. Cell pellets were resuspended in 1 ml of distilled water containing 125 μg/ml of butylated hydroxytoluene (BHT) (Sigma) as anti-oxidant and sonicated. An aliquot of 200 μl of each plasma, cell and medium sample was added to 400 μl $CH_3CN$ containing 125 μg/ml BHT, and the mixture was vortexed and centrifuged to pellet the precipitated proteins. The recovered supernatants were analyzed on a liquid chromatograph (Perkin Elmer, Norwall, Conn.) fitted with a C18 (5 μm) reverse-phase column (150×4.6 mm) and a C18 precolumn (Perkin Elmer, Milan, Italy). The mobile phase consisted of $CH_3CN:H_2O:CH_3COOH$ (75:23:2, vol/vol/vol) delivered at a flow rate of 2 ml/min. Detection was performed with a Perkin Elmer LC95 absorbance detector at 340 nm. The reference standard 4-HPR, was supplied by the R. W. Johnson Pharmaceutical Research Institute (Spring House, Pa., USA).

Identification of the polar metabolite was performed by atmospheric pressure chemical ionization mass spectrometry (APCI-MS) analysis in positive mode. APCI mass spectra were acquired using a ThermoQuest LCQDeca mass spectrometer (Finnigan Mat, San Jose, Calif., USA) equipped with an atmospheric pressure chemical ion source and an Xcalibur data system and connected to an HPLC system. The conditions of HPLC separation were the same as described above with the following modifications: the flow rate of the mobile phase was 1 ml/min and the size of the C18 column was 125×3 mm. Operating parameters of the APCI-MS interface were optimized using flow injection of 4-HPR in the mobile phase utilized for HPLC separation at a flow rate of 10 μl/min. Optimum conditions included: sheath gas flow of 80 arbitrary units, vaporized temperature of 300° C., discharge current of 6 μA, capillary voltage of 3 V, capillary temperature of 250° C., fragmentor voltage (used for collision-induced dissociation) of 30%. Mass spectra were acquired over a range m/z 200–600.

Figure 1:
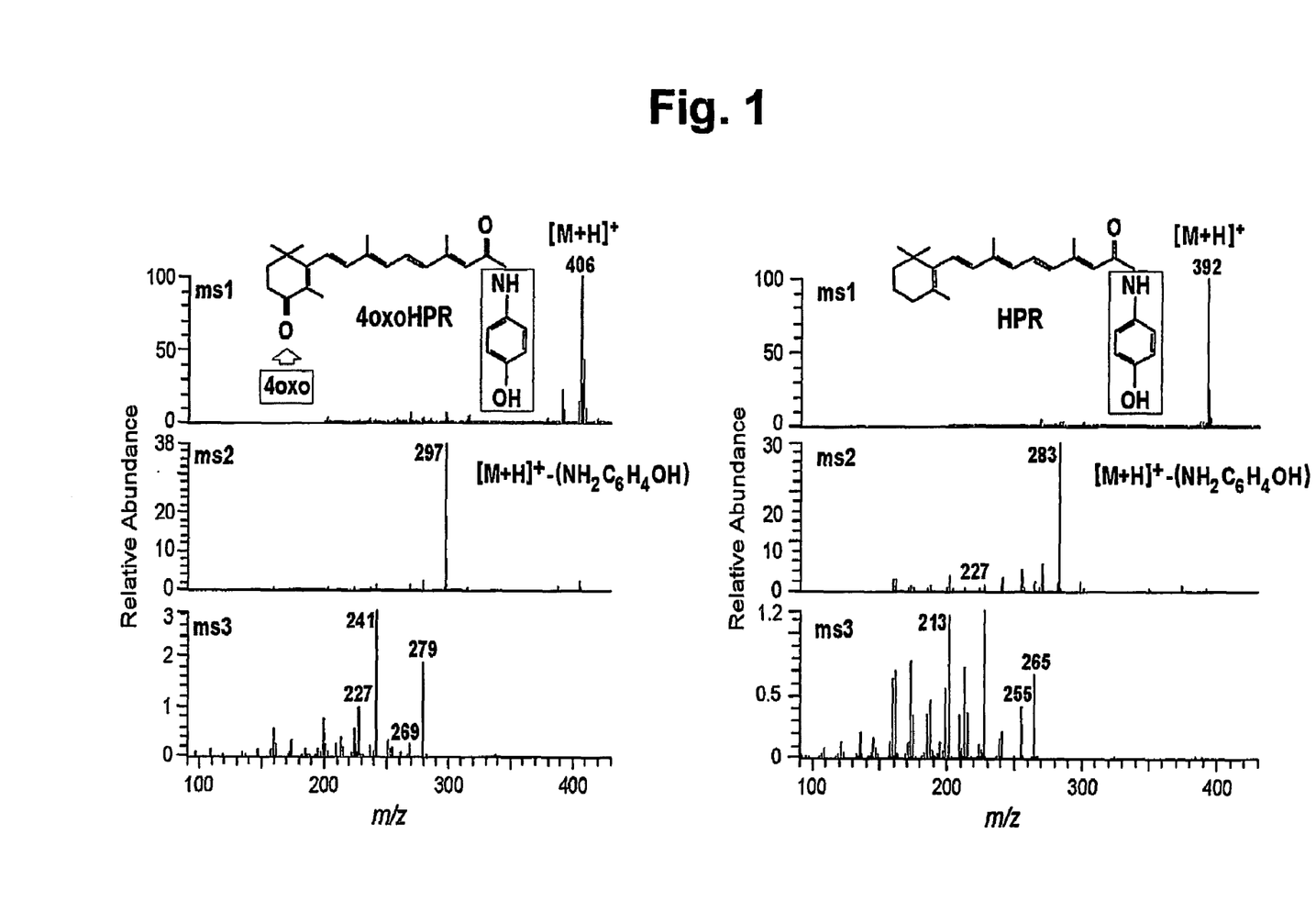
FIG. 1 shows the results of mass spectrometry analysis in positive mode for the identification of the polar metabolite.

The results of mass spectrometry analysis in positive mode are reported in FIG. 1. The polar metabolite was a compound with a positive molecular ion $[M+H]^+$ at m/z 406. Fragmentation of the positive molecular ion with m/z 406 yielded, by loss of the amino-phenyl-hydroxy group, the fragment ion $[M+H]^+—(NH_2—C_6H_4—OH)$ at m/z 297, having 14 units over the fragment ion recorded in ms2 of 4-HPR. The following fragmentation of this ion made it possible to record a ms3 spectrum containing a fragmentation pattern in which the main fragments differed again by 14 units from those present in the pattern recorded in the ms3 spectrum of 4-HPR, suggesting that 4-HPR was oxidized in the retinoic ring. The compound, by ms2 and ms3, was therefore characterized to be the 4-oxo-4-HPR.

Synthesis of 4-oxo-4-HPR

EXAMPLE 2

For the synthesis of 4-oxo-4-HPR, methyl 4-oxoretinoate was prepared as previously described (Curley and Carson, Drug Des. Del., 1987, 1:219–224) with slight modifications. That is, the unstable methyl 4-bromoretinoate was prepared as described and then treated with 9:1 acetone/water containing 1.5 equivalents of potassium carbonate, instead of the previously used potassium acetate, in order to generate methyl 4-hydroxyretinoate directly. The latter compound was then converted to 4-oxoretinoic acid as previously described. The 4-oxoretinoic acid (13 mg) was activated as its acid chloride and treated with 4-aminophenol using the method of Villeneuve and Chan Tet. Lett., 1997, 38:6489–6492.

Purification of the resultant 4-oxo-4-HPR by silica gel preparative thin-layer chromatography (1:1 ethyl acetate/hexane) gave a 28% yield (4.6 mg) of product as a yellow oil with the following properties: UV (methanol) λmax 371 nm (ε 63,210); $^1$H NMR (acetone-d6) δ 1.26 (s, 6, $(CH_3)_2$), 1.82 (s, 3,5-$CH_3$), 1.84 (t, 2,2-$CH_2$), 6.01 (s, 1, 13-H), 6.35–6.42 (m, 4, vinyls), 6.74 (d, 2, Ar, J=8.9 Hz), 7.06 (dd, 1,11-H), 7.52 (d, 2, Ar, J=8.9 Hz), 8.12 (s, 1, O/N—H), 9.03 (s, 1, O/N—H); HPLC on a Beckman Instruments (San Ramon, Calif., USA) model 127 pump with model 166 detector, using a 250×4.6 mm Ultrasphere ODS column with 85% methanol/water at 1 ml/min, tR=4.8 min (>95% purity); MS (electrospray) for $C_{26}H_{31}NO_3$+Na, calculated 428.2202, observed 428.2198. The UV spectrum was recorded on a Beckman Instruments DU-40 while $^1$H NMR spectra were recorded at 400 MHz on a Bruker Instruments (Billerica, Mass., USA) spectrometer. The MS on the synthetic material was recorded on a Micromass (Milford, Mass., USA) QTOF Electrospray mass spectrometer.

Biological Effects of 4-oxo-4HPR

Growth Inhibition of Tumor Cells

The antiproliferative activity of 4-oxo-4-HPR in human ovarian, breast, and neuroblastoma tumor cell lines was determined and compared with that of 4-HPR.

The following human ovarian carcinoma cell lines were tested: A2780 was obtained from Dr. R. F. Ozols (National Cancer Institute, Bethesda, Md., USA); IGROV-1 was obtained from Dr. J. Benard (Villejuif, France); OVCA432 was obtained from Dr. R. C. Knapp (Boston, Mass., USA); OAW42 and SKOV-3 were purchased from ATCC (Rockville, Md., USA). A2780/HPR, a 4-HPR— resistant ovarian carcinoma cell line, was obtained in our laboratory by continuous exposure of A2780 cells to increasing concentrations of 4-EPR as previously described (Appierto et al., Br. J. Cancer, 2001, 84:1528–1534; Prinetti et al., J. Biol. Chem., 2003, 278:5574–5583). Briefly, cells surviving 60 transplants in 4-HPR —containing medium (3 transplants at 1 μM, 11 transplants at 2 μM, 8 transplants at 3 μM, and 38 transplants at 5 μM) were cloned by limiting dilution. One clone, A2780/HPR, was expanded and, when tested for 4-HPR sensitivity, demonstrated a 10-fold resistance to 4-HPR, which was slightly reversible upon drug removal for five transplants. Therefore, A2780/HPR cells were continuously maintained in 5 μM 4-HPR and seeded without 4-HPR in all the experiments performed to test their sensitivity to 4-oxo-4-HPR.

The following human breast tumor cell lines, obtained from Dr. R. Sutherland (Garvan Institute, Sydney, Australia) were tested: T-47D, BT-20 and MCF-7. The following human neuroblastoma cell lines, purchased from ATCC, were tested: SK-N-BE, SK-N-SH, SK-N-MC, and GI-LI-N. All cell lines were grown in monolayer, in medium containing 10% fetal bovine serum (Invitrogen) in 5% $CO_2$ at 37° C. The medium for A2780, A2780/HPR, IGROV-1, OVCA432, SKOV-3, T-47D, BT-20, MCF-7, GI-LI-N and SK-N-BE cells was RPMI 1640 (Cambrex, Verviers, Belgium) and the medium for OAW42, SK-N-MC and SK-N-SH cells was EMEM (ATCC).

For the growth inhibition assays, cells were seeded at a density of 3500 cells per well in 96 cluster tissue culture plates, and treated 24 hr after seeding with different concentrations of 4-oxo-4-HPR or 4-HPR. 4-oxo-4-HPR was dissolved in absolute ethanol and 4-HPR (obtained from Dr. J. A. Crowell —NCI Bethesda, Md., USA) was dissolved in $Me_2SO$. 4-oxo-4-HPR and 4-HPR were dissolved at a concentration of 10 mM and stored at −800 under $N_2$ in the dark prior to further dilution in culture medium at final concentrations ranging from 0.3 to 10 μM, so that the ethanol and $Me_2SO$ concentrations did not exceed 0.1%. Control cultures received the same amount of ethanol or $Me_2SO$ as the treated cultures. 72 hr after treatment cell number was estimated by using the sulforhodamine B assay according to Monks et al., (J. Natl. Cancer, 1991, 11: 757–766). The survival of treated cells was calculated for the various drug concentrations as percentage of the survival of control cells. The antiproliferative activity of 4-oxo-4-HPR and 4-HPR in each cell line, was tested in three separate experiments and the average values ±SD are reported in FIGS. 2, 3, and 4.

Figure 2:
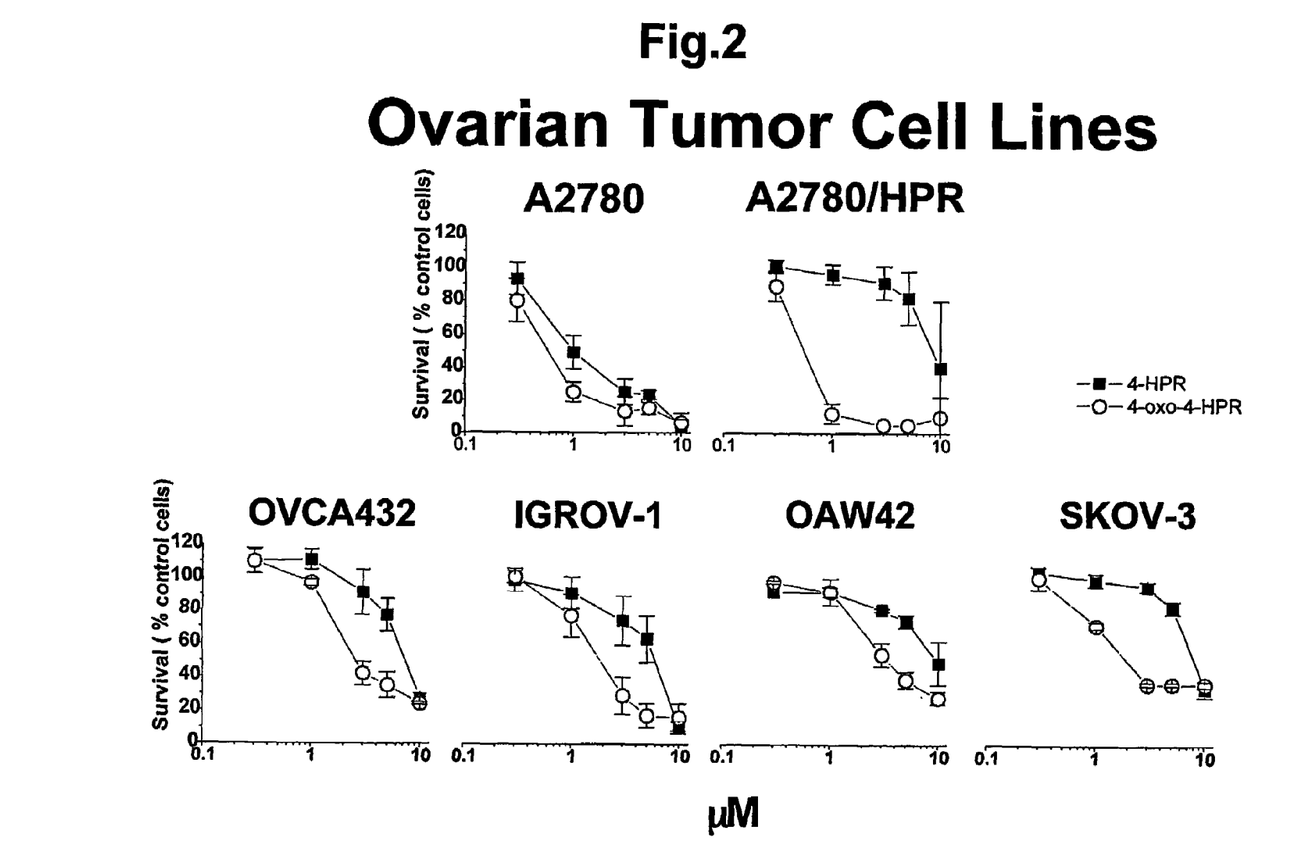
FIG. 2. reports the average values ±SD of a series of experiments concerning the antiproliferative activity of 4-oxo-4-HPR and 4-HPR in ovarian tumor cell lines.
Figure 3:
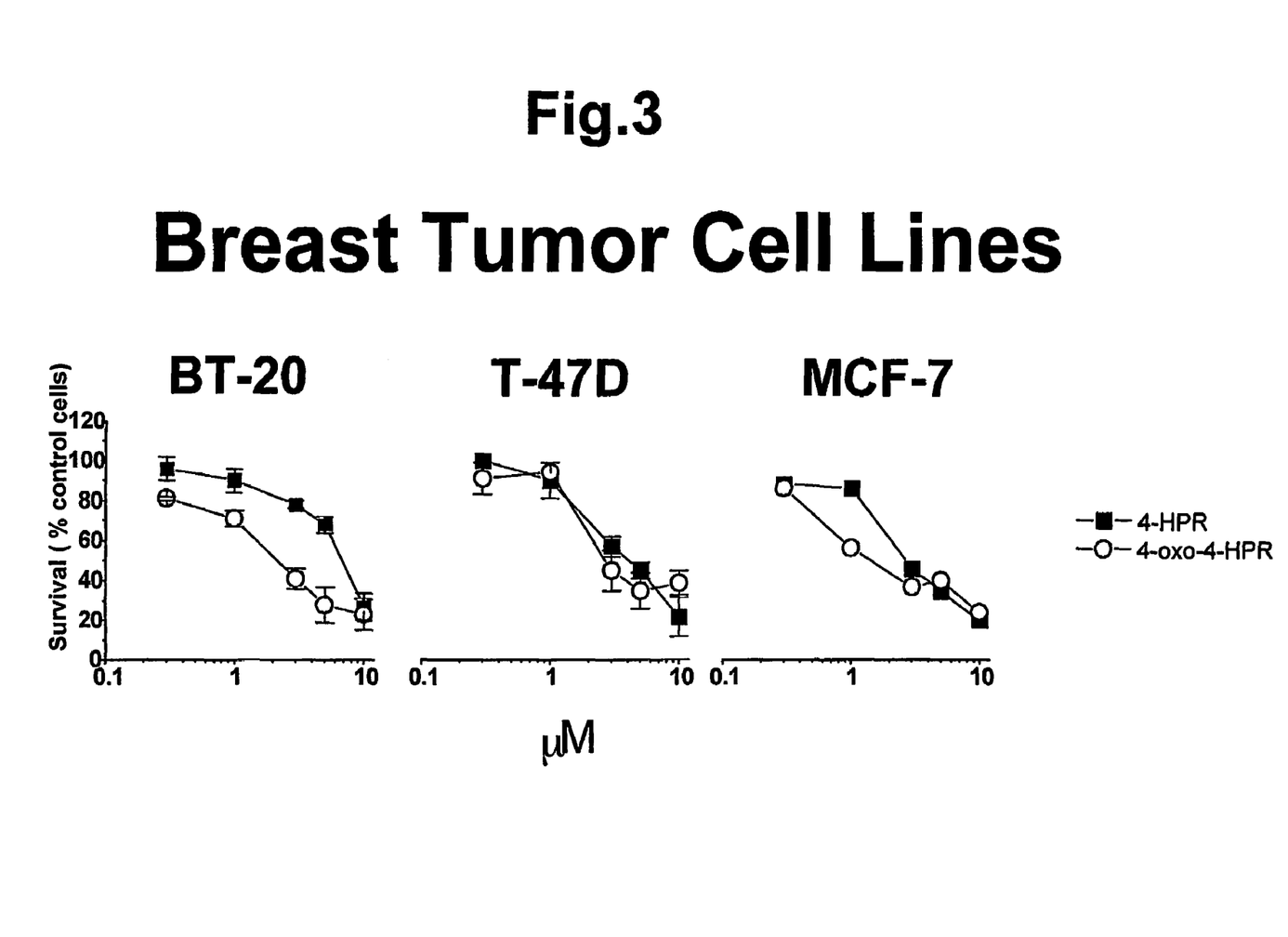
FIG. 3. reports the average values ±SD of a series of experiments concerning the antiproliferative activity of 4-oxo-4-HPR and 4-HPR in breast tumor cell lines.
Figure 4:
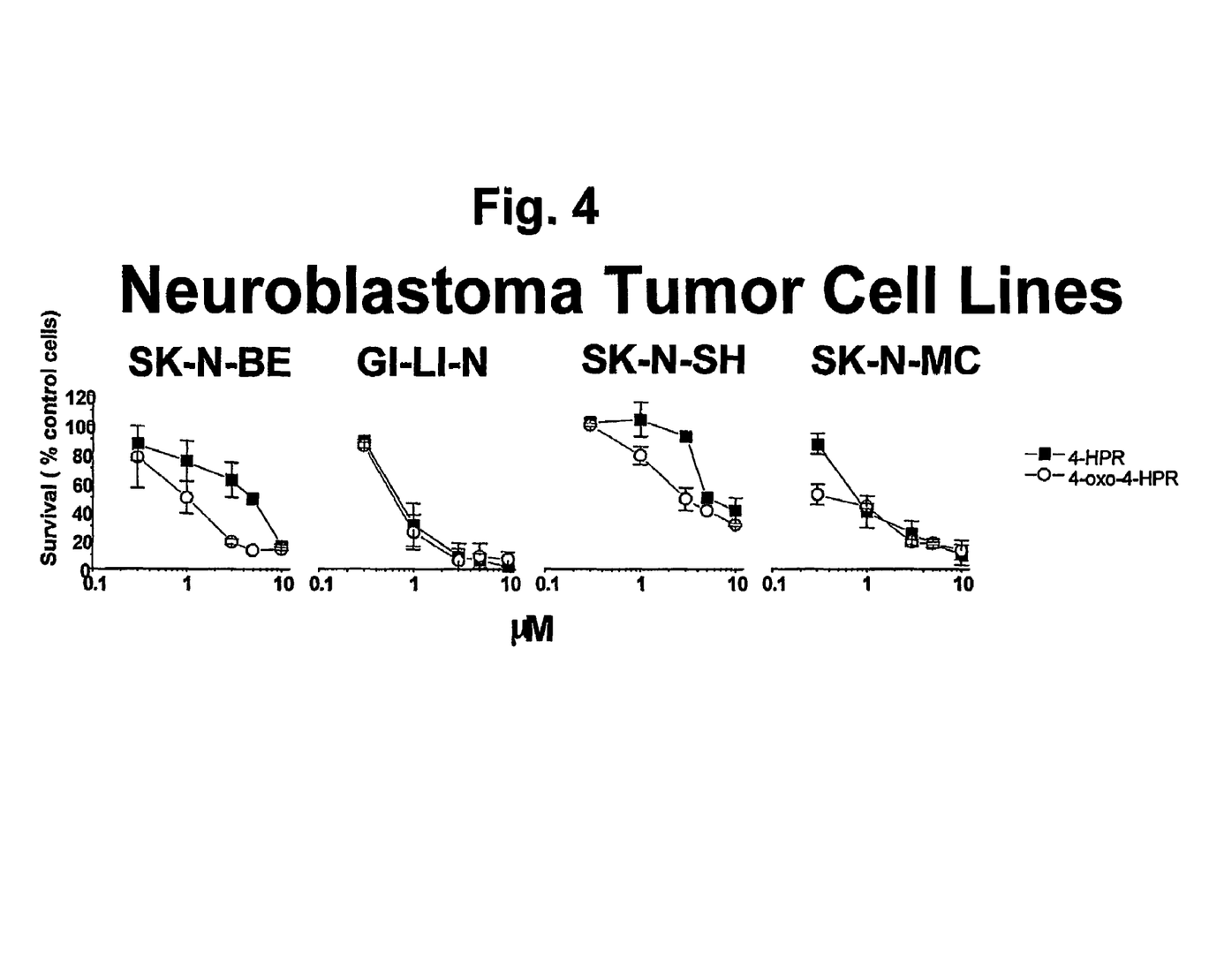
FIG. 4. reports the average values ±SD of a series of experiments concerning the antiproliferative activity of 4-oxo-4-HPR and 4-HPR in neuroblastoma tumor cell lines.

The survival of 5 ovarian tumor cell lines after treatment with various concentrations of 4-oxo-4-HPR or 4-HPR for 72 hr is reported in FIG. 2. 4-oxo-4-HPR was more effective than 4-HPR in reducing tumor cell survival in all tested cell lines. 4-oxo-4-HPR was also highly effective in A2780/HPR cells with induced resistance to 4-HPR, thus showing no cross resistance with the parent drug 4-HPR. Tested in breast tumor cell lines (FIG. 3), 4-oxo-4-HPR resulted more potent than 4-HPR in BT-20 and in MCF-7 and similarly effective in T-47D. Among the 4 tested neuroblastoma cell lines (FIG. 4), SK-N-BE and SK-N-SH were more sensitive to 4-oxo-HPR than to 4-HPR, SK-N-MC was more sensitive only at the lowest concentration tested (0.3 μM) and GI-LI-N was equally sensitive. The 50% inhibitory concentrations ($IC_{50}$) of 4-oxo-4-HPR and 4-HPR, calculated from the graphs reported in FIGS. 2, 3, and 4, are reported in Table 1.

The $IC_{50}$ of 4-oxo-4-HPR was lower than that of 4-HPR in all the tested cell lines.

Apoptosis Induction

Figure 5:
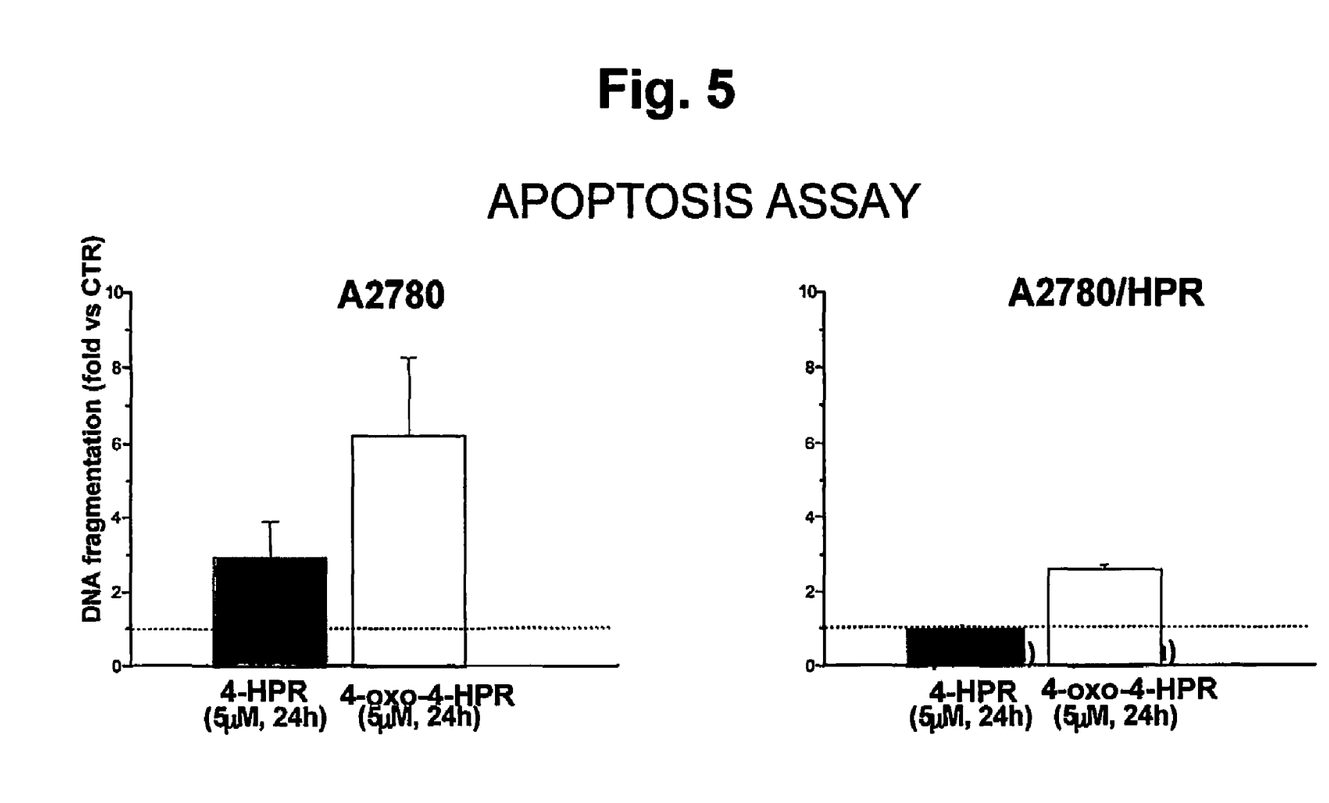
FIG. 5 reports the results of apoptosis assays, whereby DNA fragmentation in treated cells is expressed as fold versus DNA fragmentation in control cells.

Although the mechanism of action of 4-HPR is not well understood, its tumor growth inhibitory effects have been attributed to apoptosis induction (Supino et al., Int. J. Cancer, 1996, 65:491–497). The apoptosis inducing effects of 4-oxo-4-HPR were compared with those of 4-HPR in the human ovarian carcinoma cell line A2780 and in its counterpart A2780/HPR, with induced resistance to 4-HPR. Apoptosis was evaluated by a Cell Death Detection ELISA Plus Assay Kit (Roche Diagnostic GmbH, Germany) according to the manufacturer's instructions. This assay quantitates the amount of cytoplasmic histone-associated DNA fragments which increases during apoptosis. Cells were seeded in 96-well cell culture plates and treated the day after with 5 μM 4-oxo-4-HPR or 4-HPR for 24 hr. DNA fragmentation in treated cells, expressed as fold versus DNA fragmentation in control cells, is reported in FIG. 5. In A2780 cells, the induction of apoptosis by 4-oxo-4-HPR was higher than that of 4-HPR. 4-oxo-4-HPR also induced apoptosis in A2780/HPR cells, whereas 4-HPR had no effect.

Antiproliferative Effect of the Combined Treatment of 4-oxo-4-HPR with 4-HPR

Figure 6:
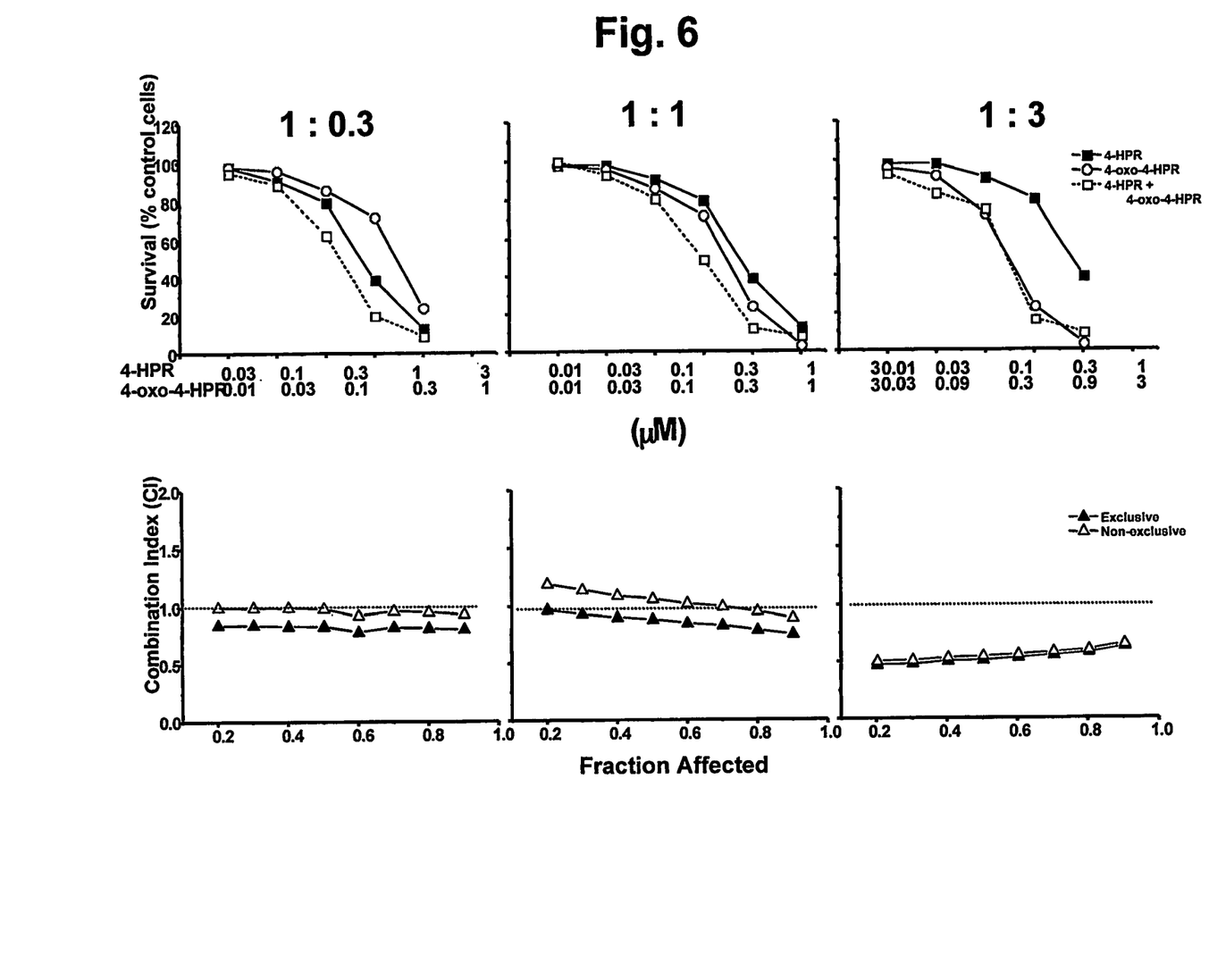
FIG. 6 reports the results of experiments carried out with the combination of 4-oxo-4-HPR and 4-HPR, showing the antiproliferative effect of the combined treatment.

Studies were performed to assess whether 4-oxo-4-HPR potentiates the tumor growth inhibitory effects of 4-HPR. A2780 cells were exposed to a range of concentrations of 4-HPR and 4-oxo-4-HPR as single agents and of both agents together at 3 different ratios, namely 1:0.3, 1:1 and 1:3. The fractional survival (f) after 3 days of treatment was calculated for each experimental condition. CalcunSyn software, based on the median-effect analysis method according to Chou and Talalay, as described in Adv. Enzyme Regul., 1984, 22:27–55, was then used to determine the effects of the combination of the 2 drugs. For each level of fractional survival (f=0.80, 0.70, . . . , 0.20, 0,10), a combination index (CI) was calculated according to the equation:

$$CI=(D)_1/(D_f)_1+(D)_2/(D_f)_2+\alpha[(D)_1(D_f)_2/(D_f)_1(D_f)_2]$$

where $(D)_1$ and $(D)_2$ are the concentrations of the combination required to produce fractional survival f, $(D_f)1$ and $(D_f)^2$ are the concentrations of the individual drugs required to produce f, and $\alpha=0$ or 1 if the drugs' mechanisms of action are mutually exclusive or mutually nonexclusive, respectively. CI<1.0 indicates synergy, CI=1.0 indicates additivity, and CI> indicates antagonism. The results of the experiments with the combination of 4-oxo-4-HPR and 4-HPR are presented in FIG. 6. At the 3 ratios tested, the combination of the two drugs resulted in a greater degree of growth inhibition compared with those obtained with the two agents alone. Using mutually exclusive assumptions, the CI values were lower than 1 at all concentrations, suggesting a synergistic interaction of the two drugs.

The antiproliferative effect of the combination of the two drugs, administered at one single dose, was also tested in other ovarian carcinoma cell lines and in breast tumor cell lines. The type of interaction between 4-HPR and 4-oxo-4-HPR was assessed by the method of Drevinko et al., as described in Cancer Biochem. Biophys., 1976, 1:187–195. For this evaluation the drugs were assumed to provide independent effects. The combination index (CI) was calculated as follows: survival fraction (SF) of the combination of 4-HPR+4-oxo-4-HPR divided by (SF 4-HPR×SF 4-oxo-4-HPR). The results for CI are defined as follows: CI=1 indicates an additive effect, CI<1 indicates a supra-additive effect and CI>1 indicates a sub-additive effect. The results of the single experiments are reported in Table 2. When doses of 4-HPR and 4-oxo-4-HPR which produced almost no growth inhibitory effects were combined, they resulted in a supra-additive effect in all but one cell lines, thus confirming that 4-oxo-4-HPR is able to potentiate 4-HPR tumor growth inhibitory effects.

Effects on Plasma Retinol

One of the main side effects of 4-HPR, is diminished dark adaptation or nyctalopia (Formelli et al., FASEB J., 1996, 10:1014–1024) which is caused by a decrease in plasma retinol levels (Formelli et al., Cancer Res., 49:6149–6152). The influence of 4-oxo-4-HPR on plasma retinol levels was assessed in mice and was compared with the effects caused by 4-HPR. Animal studies were approved by the Ethics Committee for Animal Experimentation of Istituto Nazionale Tumori (Milan Italy) and were carried out according to national and international guidelines (Italian Governing Law, Legislative decree 116, Jan. 27, 1992 and UKCCCR guidelines for the welfare of animals in experimental neoplasia. Br. J. Cancer 1988, 58:109–113). Female Swiss nude mice (7–9 weeks old) were supplied by Charles River (Calco, Italy) and kept in laminar air-flow rooms in sterilised cages, with bedding, food and acidified water. 4-HPR was obtained from Dr. J. A. Crowell —NCI Bethesda, Md., USA. 4-oxo-4-HPR and 4-HPR were dissolved in absolute ethanol and then diluted in a sterile 0.9% (w/v) NaCl solution containing 1,65 mg/ml bovine serum albumin (Sigma, St Louis, Mo., USA) at a final ethanol concentration of 10% (v/v). The drug solutions were freshly prepared once a week, protected from light and kept at 4° C. Mice were treated i.p. with 120 mg/kg of 4-oxo-4-HPR or 4-HPR for 4 days. The two drugs were delivered at a volume of 10 ml/kg of body weight. Control mice were treated with the same solvent of 4-oxo-4HPR and 4-HPR. Three mice per group were used. Blood samples, for drug and retinol measurements, were drawn from the retroorbital plexus of anesthetized mice before and 5 hr after the last treatment, collected into heparinized tubes and wrapped in aluminium foil in order to protect them from light. Retinol and drug concentrations in plasma were assayed by HPLC as previously described (Formelli et al., Cancer Res. 1989, 49:6149–6152) and as above reported (see Exemple 1) and are reported in Table 3. 4-HPR caused a remarkable (56%) reduction of plasma retinol levels, whereas 4-oxo-4-HPR was less potent and caused a reduction only slightly higher than observed in control mice.

The average plasma drug concentrations, found after administration of equal doses, were similar for the two drugs (4-oxo-4-HPR=783 ng/ml and 4-HPR=847 ng/ml). In mice treated with 4-HPR the drug was metabolized to 4-oxo-4-HPR, as observed in humans (see Exemple 1).

TABLE 1

Tumor growth inhibitory effects
50% Inhibitory Concentrations ($IC_{50}$) at 72 h

| Tumor cell lines | 4-HPR (µM) | 4-oxo-4-HPR (µM) |
|---|---|---|
| OVARIAN | | |
| A2780 | 1.5 | 0.6 |
| A2780/HPR | 8 | 0.5 |
| OVCA432 | 8 | 2.5 |
| IGROV-1 | 5 | 2 |
| OAW42 | 10 | 3 |
| SKOV-3 | 8 | 2 |
| BREAST | | |
| BT-20 | 7 | 2 |
| T-47D | 4 | 2.5 |
| MCF-7 | 3 | 1.5 |
| NEUROBLASTOMA | | |
| SK-N-BE | 5 | 1 |
| GI-LI-N | 0.7 | 0.6 |
| SK-N-SH | 5 | 3 |
| SK-N-MC | 0.7 | 0.4 |

TABLE 2

Antiproliferative effect of 4-HPR and 4-oxo-4-HPR as single agents and in combination at 72 h

| | Survival (% control cells) | | | | | |
|---|---|---|---|---|---|---|
| | 4-HPR | | 4-oxo-4-HPR | | 4-HPR + 4-oxo- | |
| Tumor cell lines | (1 µM) | (5 µM) | (0.3 µM) | (1 µM) | 4-HPR | $CI^a$ |
| OVARIAN | | | | | | |
| OVCA432 | 115 | | | 98 | 35 | 0.36 |
| | 105 | | | 102 | 53 | 0.53 |
| IGROV-1 | 97 | | | 96 | 17 | 0.18 |
| | 91 | | | 76 | 43 | 0.30 |
| SW626 | 96 | | | 90 | 55 | 0.64 |
| | 98 | | | 98 | 62 | 0.70 |
| A2780/HPR | | 81 | 96 | | 55 | 0.70 |
| | | 89 | 84 | | 35 | 0.47 |
| | | 81 | 71 | | 28 | 0.49 |

TABLE 2-continued

Antiproliferative effect of 4-HPR and 4-oxo-4-HPR as single agents and in combination at 72 h

| | Survival (% control cells) | | | | | |
|---|---|---|---|---|---|---|
| Tumor | 4-HPR | | 4-oxo-4-HPR | | 4-HPR + 4-oxo- | |
| cell lines | (1 μM) | (5 μM) | (0.3 μM) | (1 μM) | 4-HPR | CI[a] |
| BREAST | | | | | | |
| T-47D | 90 | | 94 | | 61 | 0.71 |
| BT-20 | 89 | | 70 | | 57 | 0.91 |
| MCF-7 | 86 | | 56 | | 60 | 1.25 |

[a]CI = Combination Index calculated as follows: Survival Fraction (SF) 4-HPR + 4-oxo-4-HPR / (SF 4-HPR × SF 4-oxo-4-HPR). CI = 1 additive effect; CI < 1 supra-additive or potentiation effect; CI > 1 subadditive effect.

TABLE 3

Drug levels and retinol level reduction in mice treated with 4-oxo-4-HPR and 4-HPR[a]

| | | | Retinol | | |
|---|---|---|---|---|---|
| Group of treatment | 4-HPR (ng/ml) | 4-oxo-4-HPR (ng/ml) | at baseline (ng/ml) | after treatment (ng/ml) | % reduction |
| Control | 0 | 0 | 166 ± 39 | 129 ± 30 | 22 |
| 4-oxo-4-HPR | 0 | 783 ± 117 | 176 ± 11 | 107 ± 24 | 38 |
| 4-HPR | 847 ± 117 | 355 ± 57 | 156 ± 59 | 55 ± 20 | 56 |

[a]Female Swiss nude mice were treated i.p. with 120 mg/kg of 4-oxo-4-HPR or 4-HPR for 4 days. Control mice were treated with the same solvent used for 4-oxo-4-HPR and 4-HPR. Three mice per group were used. Blood samples were collected at baseline and 5 h after the last treatment. The values are expressed as mean ±S.D.

The invention claimed is:

1. A drug consisting of a metabolite of fenretinide, or N-(4-hydroxyphenyl)retinamide (4-HPR), specifically 4-oxo-N-(4-hydroxyphenyl)retinamide (4-oxo-4-HPR) of the following formula:

2. A drug according to claim 1, further comprising fenretinide, or N-(4-hydroxyphenyl)retinamide (4-HPR).

3. A method of treating a hyperproliferative disorder in a subject in need of such treatment, comprising administering to said subject drug consisting of a metabolite of fenretinide, or N-(4-hydroxyphenyl)retinamide (4-HPR), specifically 4-oxo-N-(4-hydroxyphenyl)retinamide (4-oxo-4-HPR) of the following formula:

4. A method according to claim 3, comprising administering to said subject a combination, of 4-oxo-4-HPR and 4-HPR.

5. A method according to claims 3 or 4 in the treatment of ovarian carcinoma.

6. A method according to claims 3 or 4 in the treatment of breast tumor.

7. A method according to claims 3 or 4 in the treatment of neuroblastoma.

* * * * *